United States Patent
Lee-Chen et al.

(10) Patent No.: US 9,770,478 B2
(45) Date of Patent: Sep. 26, 2017

(54) METHOD FOR INHIBITING NEURONAL CELL AGGREGATION

(71) Applicant: NATIONAL TAIWAN NORMAL UNIVERSITY, Taipei (TW)

(72) Inventors: Guey-Jen Lee-Chen, Taipei (TW); Chiung-Mei Chen, Taipei (TW)

(73) Assignee: NATIONAL TAIWAN NORMAL UNIVERSITY (TW)

( * ) Notice: Subject to any disclaimer, the term of this patent is extended or adjusted under 35 U.S.C. 154(b) by 361 days.

(21) Appl. No.: 14/585,607

(22) Filed: Dec. 30, 2014

(65) Prior Publication Data

US 2015/0190444 A1  Jul. 9, 2015

Related U.S. Application Data

(60) Provisional application No. 61/954,787, filed on Mar. 18, 2014.

(30) Foreign Application Priority Data

Jan. 6, 2014  (TW) .............................. 103100335 A

(51) Int. Cl.
*A61K 36/48* (2006.01)
*A61K 36/484* (2006.01)
*A61K 36/185* (2006.01)

(52) U.S. Cl.
CPC ................................ *A61K 36/484* (2013.01)

(58) Field of Classification Search
None
See application file for complete search history.

(56) References Cited

U.S. PATENT DOCUMENTS

2004/0253647 A1* 12/2004 Mathews ........... G01N 33/5008
                                                        435/7.2
2014/0114216 A1*  4/2014 Konofagou ............ A61B 8/481
                                                        601/2

OTHER PUBLICATIONS

Kuo-Hsuan Chang, Wan-Ling Chen, Li-Ching Lee, Chih-Hsin Lin, Pin-Jui Kung, Te-Hsien Lin, Yi-Ci Wu, Yih-Ru Wu, Yi-Chun Chen, Guey-Jen Lee-Chen, and Chiung-Mei Chen, "Aqueous Extract of Paeonia lactiflora and Paeoniflorin as Aggregation Reducers Targeting Chaperones in Cell Models of Spinocerebellar Ataxia 3", vol. 2013, pp. 1-11.
Na Li, Ji-Hua Liu, Jian Zhang, and Bo-Yang Yu, "Comparative Evaluation of Cytotoxicity and Antioxidative Activity of 20 Flavonoids", J. Agric. Food Chem. 2008, 56, pp. 3876-3883.
Isabella Irrcher, Vladimir Ljubicic, Angie F. Kirwan, David A. Hood, "AMP-Activated Protein Kinase-Regulated Activation of the PGC-1α Promoter in Skeletal Muscle Cells", Oct. 2008, vol. 3, Issue 10.
Chiung-Mei Chen, Yu-Ting Weng, Wan-Ling Chen, Te-Hsien Lin, Chih-Ying Chao, Chih-Hsin Lin, I-Cheng Chen, Li-Ching Lee, Hsuan-Yuan Lin, Yih-Ru Wu, Yi-Chun Chen, Kuo-Hsuan Chang, Hsiang-Yu Tang, Mei-Ling Cheng, Guey-Jen Lee-Chen, Jung-Yaw Lin, "Aqueous extract of Glycyrrhiza inflata inhibits aggregation by upregulating PPARGC1A and NFE2L2—ARE pathways in cell models of spinocerebellar ataxia 3", Free Radical Biology and Medicine 71 (2014) pp. 339-350.
Meenakshi Verma, Abhishek Sharma, Swarna Naidu, Ankan Kumar Bhadra, Ritushree Kukreti, Vibha Taneja, "Curcumin Prevents Formation of Polyglutamine Aggregates by Inhibiting Vps36, a Component of the ESCRT-II Complex", Aug. 2012, vol. 7, Issue 8.

* cited by examiner

*Primary Examiner* — Chris R Tate
*Assistant Examiner* — Randall Winston
(74) *Attorney, Agent, or Firm* — Bacon & Thomas, PLLC

(57) ABSTRACT

The invention relates to a novel use of the Chinese herb *Glycyrrhiza inflata* in treatment of neurodegenerative disorders. Particularly, the invention relates to the use of ammonium glycyrrhizinate and licochalcone A in targeting polyQ-mediated spinocerebellar ataxia.

16 Claims, 9 Drawing Sheets

METHOD FOR INHIBITING NEURONAL CELL AGGREGATION

CROSS REFERENCE TO RELATED APPLICATION

This application claims the benefits of the Taiwan Patent Application Serial Number 103100335, filed on Jan. 6, 2014, the subject matter of which is incorporated herein by reference.

This application also claims the benefit of filing date of U.S. Provisional Application Ser. No. 61/954,787, entitled "NEW USE OF *GLYCYRRHIZA INFLATA* IN TREATMENT OF NEURODEGENERATIVE DISORDERS" filed Mar. 18, 2014.

BACKGROUND OF THE INVENTION

1. Field of the Invention

The invention relates to a novel use of *Glycyrrhiza inflata* (*G. inflata*) extract in treatment of neurodegenerative disorders. Particularly, the invention relates to the use of ammonium glycyrrhizinate (AMGZ) and licochalcone A contained in the extract in treating polyglutamine (polyQ)-mediated spinocerebellar ataxia (SCA).

2. Description of Related Art

Most age-related neurodegenerative diseases, such as Alzheimer's disease (AD) and Parkinson's disease (PD), are characterized by accumulation of aberrant protein aggregates/inclusions in the affected brain regions. Among them, SCA types 1, 2, 3, 6, 7, 8, 17, and dentatorubropallidoluysianatrophy (DRPLA) as well as Huntington's disease (HD) are a group of neurodegenerative disorders caused by expanded CAG repeats encoding a long polyQ tract in the respective proteins. The polyQ-mediated SCAs have shown selective progressive degeneration of the cerebellum, brainstem, and spinal tract, with pathological hallmark of intranuclear and cytoplasmic aggregates. Impaired proteasome and autophagy activity, transcriptional dysregulation, oxidative stress, and mitochondrial dysfunction have been shown to play important roles in the pathogenesis of polyQ-mediated diseases. Increasingly substantial evidence has shown that aggregate formation promoted by misfolding of the polyQ protein is likely the initial process to trigger the subsequent pathological events. Therefore, agents that can prevent the aggregate formation or promote the degradation of aggregates may possess the great potential to treat the polyQ diseases.

Peroxisome proliferator-activated receptor gamma, coactivator 1 alpha (PPARGC1A) is a known regulator of mitochondrial biogenesis and anti-oxidative response genes, such as superoxide dismutase 2 (SOD2) and mitochondrial and cytochrome c, somatic (CYCS). PPARGC1A null mice developed spongiform neurodegeneration in selective brain areas, which indicated the direct role of PPARGC1A in neurodegeneration. Transcriptional repression of PPARGC1A by mutant huntington leading to mitochondrial dysfunction and neurodegeneration has also been shown in HD mouse models, suggesting that agents enhancing the transcriptional activity of PPARGC1A may be the potential therapeutics for HD and other polyQ diseases.

Increased oxidative damage plays an important role in the pathogenesis of SCA1, SCA2, SCA3, SCAT, SCA17, HD, and other expanded polyQ diseases. Anti-oxidants have been shown to be the potential therapeutics for SCA1, SCA17 and HD. The nuclear factor erythroid 2-related factor 2 (NFE2L2) and the antioxidant response elements (AREs) signaling pathway is regarded as the most important in the cell to protect against oxidative stress. The principal transcription factor NFE2L2 binds to AREs and recruits the general transcriptional machinery for ARE-dependent gene expression when the cells respond to oxidative stress. The endogenous phase II anti-oxidative enzymes, heme oxygenase (decycling) 1 (HMOX1), NAD(P)H dehydrogenase, quinone 1 (NQO1), glutamate-cysteine ligase catalytic subunit (GCLC), and glutathione S-transferase pi 1 (GSTP1) are among the target genes regulated by NFE2L2. NFE2L2 plays a neuroprotection role in the MPTP mouse model of PD. Mutant huntington disrupts NFE2L2 signaling, which contributes to impaired mitochondrial dynamics and may enhance susceptibility to oxidative stress in a HD cell model. PPARGC1A was recently found to also regulate the transcription of NFE2L2. Therefore, we proposed that compounds that can activate PPARGC1A and/or NFE2L2 may be beneficial to SCA3 and other polyQ diseases. The roots of licorice (*Glycyrrhiza*) species have long been used as an herbal medicine to treat peptic ulcer, hepatitis C, diabetes, and pulmonary and skin diseases. *G. inflata* is one of *Glycyrrhiza* species. Licochalcone A and glycyrrhizin, two major constituents of *G. inflata* have recently been reported to have anti-oxidative, anti-inflammatory, anti-microbial as well as neuroprotective effects.

Although there are prior art references disclosing relationship between the anti-oxidants and SCAs, none of them is relevant to the *G. inflata* extract and the correlation of *G. inflata* extract with SCAs remains unclear. Therefore, it is beneficial to develop a medicament based on *G. inflata* for treatment of neurodegenerative disorders.

SUMMARY OF THE INVENTION

An object of the present invention is to provide a method for inhibiting neuronal cell aggregation, to thereby serve as an adjuvant therapy for neurodegenerative disease, such as spinocerebellar atrophy.

To achieve the above objects, the present invention provides a method for inhibiting neuronal cell aggregation, comprising contacting the neuronal cell with an effective amount of *G. inflata* extract. The *G. inflata* extract comprises AMGZ or licochalcone A, wherein AMGZ and licochalcone A are the active ingredients extracted from *G. inflata*. *G. inflata* extract, AMGZ, and licochalcone A are all commercially available.

In addition, the *G. inflata* extract has the function of enhancing mitochondrial biogenesis and reducing reactive oxygen species (ROS). In the polyQ-mediated diseases, the misfolded polyQ causes increased reactive oxygen species and accumulation of abnormal polyQ proteins. Accordingly, the *G. inflata* reduces the accumulation of polyQ by enhancing mitochondrial biogenesis and reducing ROS through increasing PPARGC1A (peroxisome proliferator-activated receptor gamma coactivator 1-alpha) and NFE2L2 (nuclear factor (erythroid-derived 2)-like 2) protein expression, and in turn, increasing the expression of the downstream proteins, such as NQO1 (NAD(P)H dehydrogenase (quinone 1)), GCLC (glutamate-cysteine ligase catalytic subunit), GSTP1 (glutathione S-transferase pi 1), SOD2 (superoxide dismutase 2), and CYCS (cytochrome c, somatic).

In SCAs, the expansions of translated CAG repeats in the disease genes result in long polyQ tracts in the respective proteins. The accumulation of intranuclear and cytoplasmic misfolded polyQ proteins is thought to induce oxidative stress and lead to cell death. Thus, suppression of aggregation and reducing ROS are expected to inhibit a wide range of harmful downstream events, providing an observation for identifying the potential treatments of SCA. In the present invention, we established a high-throughput aggregation screening system using 293 ATXN3/$Q_{75}$-GFP cells, and applied this system in testing the aqueous extract of *G. inflata* and its constituents. We found that the aggregation can be significantly prohibited by *G. inflata* and its active components AMGZ and licochalcone A. Meanwhile, *G. inflata*, AMGZ and licochalcone A enhanced mitochondrial biogenesis and antioxidative activity in the same cell models. All of them further reduced the aggregation in neuronal differentiated SH-SY5Y ATXN3/$Q_{75}$-GFP cells. The present invention demonstrates how *G. inflata*, AMGZ and licochalcone A are likely to work on polyQ-aggregation reduction, and provides insight into the possible working mechanism of *G. inflata* in SCA patients. These finding suggests that *G. inflata*, licochalcone A, and AMGZ may be a potential candidate for the treatment of SCA3 and other polyQ-mediated diseases.

Other objects, advantages, and novel features of the invention will become more apparent from the following detailed description when taken in conjunction with the accompanying drawings.

DETAILED DESCRIPTION OF THE PREFERRED EMBODIMENT

Figure 1A:
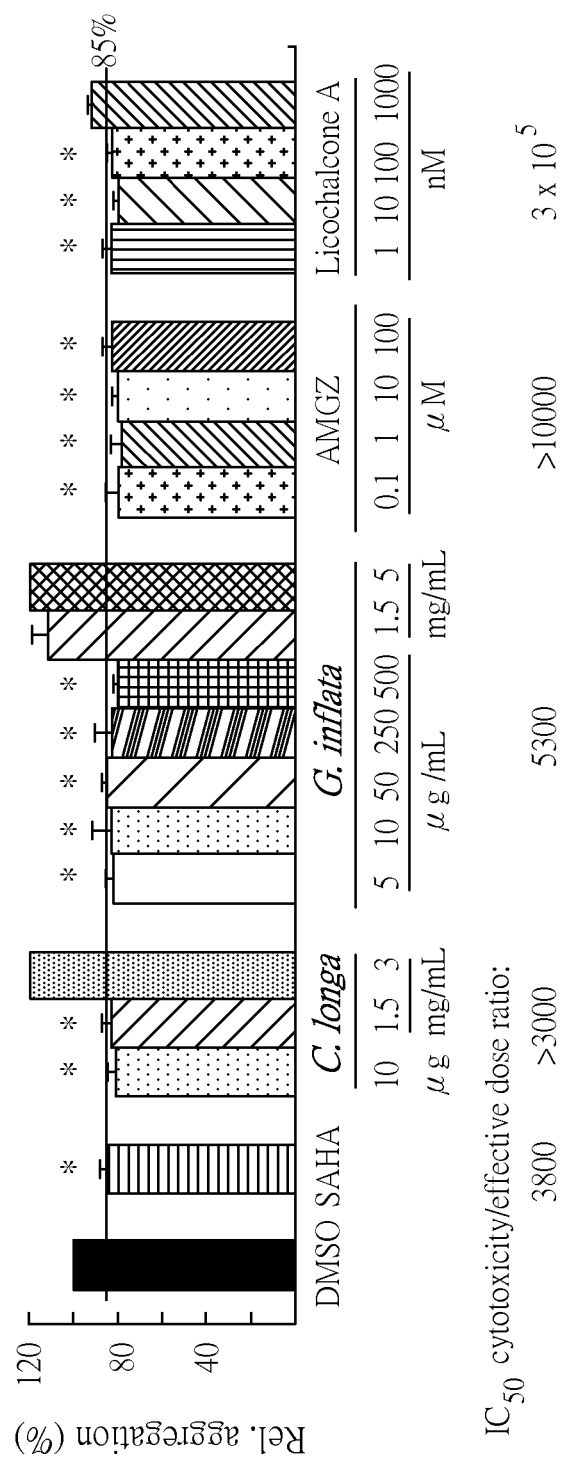
FIG. 1a shows the aggregation analysis of ATXN3/$Q_{75}$-GFP cells untreated or treated with *C. longa* extract, *G. inflata* extract, suberoylanilide hydroxamic acid (SAHA), AMGZ and licochalcone A according to a preferable example of the present invention.

In the following description, numerous specific details are set forth to provide a thorough understanding of embodiments of the present disclosure. However, one having an ordinary skill in the art will recognize that embodiments of the disclosure can be practiced without these specific details. In some instances, well-known structures and processes are not described in detail to avoid unnecessarily obscuring embodiments of the present disclosure.

The invention surprisingly found that *G. inflata* extract and its components, licochalcone A and AMGZ, inhibit the aggregation of 293 ATXN3/$Q_{75}$-GFP cells and promote the biogenesis of mitochondria. In addition, all of *G. inflata* extract, licochalcone A and AMGZ further reduced the aggregation in neuronal differentiated SH-SY5Y ATXN3/$Q_{75}$-GFP cells. The invention further suggests that the aggregate-inhibitory effect of *G. inflata* extract, licochalcone A, and AMGZ is mediated through activating PPARGC1 and NFE2L2 and their downstream target genes expression. The present invention proves that *G. inflata*, licochalcone A, and AMGZ may be a novel alternative therapeutic agent for SCA3 and other polyQ-mediated diseases.

All scientific and technical terms used in this application have meanings commonly used in the art unless otherwise specified. As used in this application, the following words or phrases have the meanings specified.

The terms "a" and "an" refer to one or to more than one (i.e., to at least one) of the grammatical object of the article.

The term "expression" when used in the context of expression of a gene or nucleic acid refers to the conversion of the information contained in a gene into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include messenger RNAs which are modified by processes such as capping, polyadenylation, methylation, and editing, and proteins modified by, for example, methylation, acetylation, phosphorylation, ubiquitination, ADP-ribosylation, myristoylation, and glycosylation.

The terms "promote," "promotion," and "promoting" refer to an increase in an activity, response, condition, disease or other biological parameter. The term "promoting mitochondrial biogenesis" refers to augmenting, improving, increasing, or inducing biogenesis of mitochondria.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the active ingredient of the invention to perform their intended function.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The term "effective amount" means an amount of *G. inflata* extract, licochalcone A or AMGZ which is effective to treat and/or prevent aggregate formation or promote mitochondrial biogenesis.

In one aspect, the invention provides a method for inhibiting neuronal cell aggregation, comprising contacting the neuronal cell with an effective amount of *G. inflata* extract. The method of the present invention may be performed in vivo or in vitro.

In one embodiment, the method of the present invention is performed in a subject in need thereof. Preferably, the subject is a human.

In one embodiment, the *G. inflata* extract comprises AMGZ or licochalcone A. In one embodiment, the *G. inflata* extract comprises AMGZ. In another embodiment, the *G. inflata* extract comprises licochalcone A. The chemical structures of AMGZ and licochalcone A are known as follows:

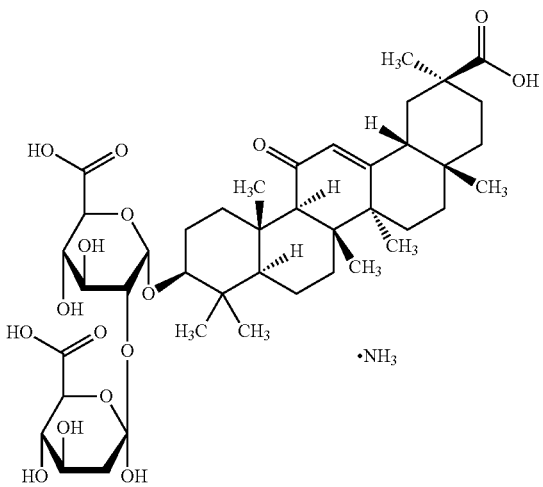

Ammonium glycyrrhizinate (AMGZ)
Molecular Formula: $C_{42}H_{62}O_{16} \cdot NH_3$
Average mass: 839.96 Da

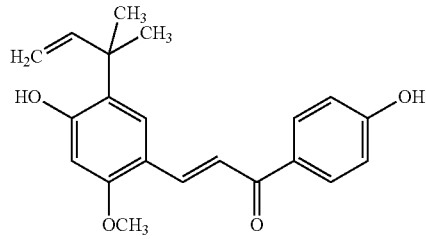

Licochalcone A
Molecular Formula: $C_{21}H_{22}O_4$
Molecular mass: 338.40 Da

An "effective amount" of *G. inflata* extract, as described above, refers to a sufficient amount of *G. inflata* extract, or AMGZ or licochalcone A, to inhibit neuronal cell aggregation at a reasonable benefit/risk ratio applicable to any treatment. In one embodiment, an effective amount of the *G. inflata* extract is supplied at a dosage level of 5~500 µg/mL. In one embodiment, an effect amount of AMGZ is 0.1~100 µM. In one embodiment, an effect amount of licochalcone A is 0.001~0.1 µM.

In one embodiment, the method of the present invention inhibits neuronal cell aggregation through enhanced PPARGC1A expression. In one embodiment, the enhanced PPARGC1A expression up-regulates the downstream SOD2 and CYCS expressions to mediate mitochondrial biogenesis. In one embodiment, enhanced NFE2L2 expression up-regulates HMOX1, NQO1, GCLC and GSTP1 expressions to battle the oxidative stress.

In one embodiment, the method of the present invention inhibits neuronal cell aggregation through reduced ROS production. In one embodiment, the reduced ROS production is mediated through the radical scavenging activity of the *G. inflata* extract or licochalcone A comprised therein.

The term "neuronal cell aggregation" can occur in vivo or in vitro. The neuronal cell aggregation can be the aggregation observed in tissue culture or an aggregation found in the brain of a subject through medical diagnosis. The aggregation to be inhibited, or treated, by the invention may be mediated through, but are not limited to, the following: expanded poly-Q, Aβ, tau, α-synuclein and other misfolded proteins. For example, the method of the invention may be used to treat neuronal cell aggregation which causes SCA types 1, 2, 3, 6, 7, 8, 17, DRPLA, HD, AD or PD.

In one embodiment, the neuronal cell aggregation is poly-Q mediated. Preferably, the poly-Q mediated neuronal cell aggregation leads to a neuron degenerative disease selected from SCA types 1, 2, 3, 6, 7, 8, 17, DRPLA, HD, AD or PD. More preferably, the neuron degenerative disease is SCA. Still preferably, the neuron degenerative disease is SCA type 3.

The active ingredient of the invention (i.e., the *G. inflata* extract, or AMGZ and licochalcone A) may be formulated as various compositions and administered in a number of ways. For example, administration may be parenteral (for example by intravenous drip, subcutaneous, intraperitoneal or intramuscular injection) or oral. Multiple doses can also be administered. It will be understood, however, that the total daily usage of the active ingredients and compositions of the present invention will be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age; body weight; general health; sex and diet of the patient; the time of administration; route of administration; rate of excretion of the specific compound employed; the duration of the treatment; drugs used in combination or coincidental with the specific drug employed; and like factors well-known in the medical arts. For example, it is well within the skill of the art to start doses of the active ingredient at levels lower than those required to achieve the desired therapeutic effect and to gradually increase the dosage until the desired effect is achieved.

Any of the above-mentioned compounds can be combined with a pharmaceutically acceptable carrier to form a formulation, composition, combination or preparation (each term can be used interchangeably). The phrase "pharmaceutically acceptable carrier" used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported to the brain. Each carrier must be "acceptable" in the sense of being compatible with the other ingredients of the formulation and not injurious to the patient. Some examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

The pharmaceutical formulations of the invention may additionally contain other adjunct components conventionally found in pharmaceutical compositions/formulations, at their art-established usage levels. Thus, for example, the compositions/formulations may contain additional, compatible, pharmaceutically-active materials such as dyes, flavoring agents, preservatives, antioxidants, opacifiers, thickening agents and stabilizers. However, such materials, when added, should not unduly interfere with the biological activities of the therapeutic compounds of the invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the therapeutic compounds of the formulation. Additionally, it will be appreciated that other pharmaceutical formulations, which can conveniently be presented in unit dosage form, can be prepared according to conventional techniques well known in the pharmaceutical industry. In general, such techniques include the step of bringing into association the active ingredients with the pharmaceutical carrier(s) or excipient(s). The formulations are typically prepared by uniformly and intimately bringing into association the active ingredients with liquid carriers or finely divided solid carriers or both, and then, if necessary, shaping the product.

In addition to the active ingredient of the invention is formulated for oral or parenteral administration, such as intravenous or intramuscular injection, other pharmaceutically acceptable forms may be performed.

Optionally, one or more other conventional agents against neuronal cell aggregation (e.g. growth factors, peptides, proteolytic inhibitors, extracellular matrix components, fragments and peptides, steroids, cytokines, oxygen donators or vitamins) may also be used in the manufacture of a medicament in combination with the *G. inflata* extract, licochalcone A or AMGZ according to the invention. Such conventional wound healing agents may also be used in the method of the present invention. The inclusion of these agents may allow a synergistic effect on inhibiting neuronal cell aggregation. Such additional wound healing agent(s) may be administered separately, simultaneously or sequentially with the active ingredient of the invention. Thus, in one embodiment an effective dose of the active ingredient may be delivered in conjunction with or alternating with another effective agents against neuronal cell aggregation from the following groups: growth factors, peptides, proteolytic inhibitors, extracellular matrix components, fragments and peptides, steroids, cytokines, oxygen donators and vitamins. In one embodiment, the patient may be administered the active ingredient of the invention and the additional agent(s) against neuronal cell aggregation by means of a single medicament which comprises both the active ingredient of the invention and the additional agent(s) against neuronal cell aggregation. In another embodiment, the patient is administered the active ingredient of the invention and the additional agent(s) against neuronal cell aggregation separately.

The *G. inflata* extract, licochalcone A and AMGZ can inhibit neuronal cell aggregation. Particularly, licochalcone A is applied to a subject suffering from SCA type 3.

It will be understood that the invention has been described by way of example only and modifications may be made whilst remaining within the scope and spirit of the invention.

EXAMPLE

Materials and Methods

Herbal Extract Preparation and HPLC Analysis

Aqueous extracts from *G. inflata* and *C. longa* were provided by Sun-Ten Pharmaceutical Company (Taipei, Taiwan) as described in Chen, C. M.; Weng, Y. T.; Chen, W. L.; Lin, T. H.; Chao, C. Y.; Lin, C. H.; Chen, I. C.; Lee, L. C.; Lin, H. Y.; Wu, Y. R.; Chen, Y. C.; Chang, K. H.; Tang, H. Y.; Cheng, M. L.; Lee-Chen, G. J.; Lin, J. Y. Aqueous extract of *Glycyrrhiza inflata* inhibits aggregation through upregulating PPARGC1A and NFE2L2-ARE pathways in cell models of spinocerebellar ataxia 3. *Free Radical Biology & Medicine* 71:339-350; 2014. High pressure liquid chromatography (HPLC) was performed using a LaChrom Elite HPLC system (Hitachi), consisting of a photo diode array detector. The chromatographic separation of *G. inflata* extract (50 µL, 1 mg/mL) was carried out on a Hypersil ODS (C18) column (250×4.6 mm, 5 µm), eluted with the mixture of (A) 0.04% formic acid in water and (B) acetonitrile. The linear gradient elution program used was as follows: 20% B (0-4 min), 20-38% B (4-20 min), 38-55% B (20-25 min), 55-90% B (25-38 min), 90% B (38-50 min), 20% B (50-65 min) with a flow rate of 1 mL/min. The column and auto-sampler were maintained at 30 and 10° C., respectively. Absorbance was monitored at 250 and 368 nm, and the scan range for photo diode array was 190~400 nm. AMGZ and licochalcone A (50 μL, 0.01~1 mM) (Sigma) were used as reference compounds for *G. inflata*. *C. longa* which contains the active ingredient curcumin is a Chinese herbal medicine known to be able to inhibit polyglutamine aggregation (Verma, M.; Sharma, A.; Naidu, S.; Bhadra, A. K.; Kukreti, R.; Taneja, V. Curcumin prevents formation of polyglutamine aggregates by inhibiting Vps36, a component of the ESCRT-II complex. *PLoS One* 7:e42923; 2012). *C. longa* does not contain the two active ingredient of the present invention and is used herein for comparison with *G. inflata*.

Cell Culture and Cell Proliferation Assay

Human embryonic kidney HEK-293 cells (ATCC No. CRL-1573) and human neuroblastoma SH-SY5Y cells (ATCC No. CRL-2266) were maintained as described in Chang, K. H.; Chen, W. L.; Lee, L. C.; Lin, C. H.; Kung, P. J.; Lin, T. H.; Wu, Y. C.; Wu, Y. R.; Chen, Y. C.; Lee-Chen, G. J.; Chen, C. M. Aqueous extract of *Paeonia lactiflora* and paeoniflorin as aggregation reducers targeting chaperones in cell models of spinocerebellar ataxia 3. *Evidence-based Complementary and Alternative Medicine* 2013:471659; 2013. Cell proliferation was measured based upon the reduction of 3-(4,5-dimethylthiazol-2-yl]-2,5-diphenyltetrazolium bromide (MTT). Briefly, $5 \times 10^4$ cells were plated into 48-well dishes, grown for 20 hr and treated with herbal extract (5~30 mg/mL *G. inflata* or *C. longa*) or pure compound (100 nM~1 mM AMGZ or licochalcone A). After one day, 20 μL MTT (5 mg/mL in PBS, Sigma) was added to cells and incubated for 2 hr. The absorbance of the insoluble purple formazan product was measured at 570 nm by a Bio-Tek μQuant Universal Microplate Spectrophotometer.

ATXN3 cDNA Constructs and Isogenic Cell Lines

The cloning of plasmids containing GFP-tagged ATXN3 (ataxin 3) C-terminal fragment and the establishment of Flp-In 293 and SH-SY5Y cells with ATXN3/$Q_{75}$-GFP expression in an inducible fashion were as described in Chang, K. H.; Chen, W. L.; Lee, L. C.; Lin, C. H.; Kung, P. J.; Lin, T. H.; Wu, Y. C.; Wu, Y. R.; Chen, Y. C.; Lee-Chen, G. J.; Chen, C. M. Aqueous extract of *Paeonia lactiflora* and paeoniflorin as aggregation reducers targeting chaperones in cell models of spinocerebellar ataxia 3. *Evidence-based Complementary and Alternative Medicine* 2013:471659; 2013. These cell lines were grown in medium containing 5 μg/mL blasticidin and 100 μg/mL hygromycin (InvivoGen).

ATXN3/$Q_{75}$ Aggregation Assay

293 ATXN3/$Q_{75}$-GFP cells were plated into 96-well ($2 \times 10^4$/well) dishes, grown for 24 hr and treated with different concentrations of the *G. inflata* (5~5000 μg/mL) or *C. longa* (10~3000 μg/mL) extract, suberoylanilide hydroxamic acid (SAHA, 100 nM, Cayman Chemical), AMGZ (0.1~100 μM) and licochalcone A (1~1000 nM) for 8 hr. Then doxycycline (10 μg/mL, BD) and oxaliplatin (5 μM, Sigma) were added for 6 days. After that, cells were stained with Hoechst 33342 (0.1 μg/mL, Sigma) and aggregation percentage was assessed by a high-content analysis (HCA) system, with excitation/emission wavelengths at 482/536 (EGFP).

Glycyrrhizin is metabolized to 18β-glycyrrhetinic acid by intestinal bacteria. Therefore, ATXN3/$Q_{75}$ aggregation assay was further performed with different concentrations of the 18β-glycyrrhetinic acid (0.1~10 μM) and SAHA (0.1 μM) by the aforementioned method, aggregation percentage was assessed by HCA system.

SH-SY5Y ATXN3/$Q_{75}$-GFP cells were seeded in 6-well ($2 \times 10^5$/well) plate, with all trans retinoic acid (10 μM, Sigma) added at seeding time. At day 2, cells were treated with *G. inflata* or *C. longa* extract (10 μg/mL), AMGZ (0.2 μM) or licochalcone A (2 nM) for 8 hr, and then doxycycline (5 μg/mL) was added to induce ATXN3/$Q_{75}$-GFP expression. After one week, cells were stained with Hoechst 33342 and aggregation percentage was assessed as described. The morphologic differentiation of untreated cells including total outgrowth, processes, and branches was assessed by using HCA system.

In experiments examining the role of PPARGC1A in reducing ATXN3/$Q_{75}$ aggregation, HEK-293T cells were plated into 12-well ($2 \times 10^5$/well) dishes, grown for 20 hr, treated with *G. inflata* extract (10 μg/mL) for 8 hr, and co-transfected with the ATXN3/$Q_{75}$-GFP plasmid (1.5 μg) and control or PPARGC1A siRNA (50 pmol) (sc-38884, Santa Cruz). The cells were grown for 48 hr. Cells were stained with Hoechst 33342 and aggregation percentage was measured by using HCA system as described.

Caspase 3 Activity Assay

Caspase 3 activity was measured with the Caspase 3 Assay Kit according to the manufacturer's instructions (Sigma). Briefly, cells ($10^6$) were incubated with lysis buffer (100 μl) on ice for 20 min After centrifugation, proteins in supernatants were quantified and caspase 3 activity was measured using acetyl-Asp-Glu-Val-Asp-7-amido-4-methylcoumarin (Ac-DEVD-AMC) as substrate. The release of the fluorescent AMC was recorded in an FLx800 microplate fluorescence reader (Bio-Tek) at 360 nm excitation filter in conjunction with 460 nm emission filter. The caspase 3 activity was calculated using an AMC standard curve.

Flp-In 293 PPARGC1A Reporter Cells and Fluorescent Assay

A mCherry reporter driven by PPARGC1A promoter (−1136~+5) (see Irrcher, I.; Ljubicic, V.; Kirwan, A. F.; Hood, D. A. AMP-activated protein kinase-regulated activation of the PGC-1α promoter in skeletal muscle cells. *PLoS One* 3:e3614; 2008) was first constructed in pAmCyan1-N1. The fragment containing the PPARGC1A driven reporter was excised with AseI and NotI restriction enzymes and used to replace an AseI-NotI fragment in pcDNA5/FRT/TO plasmid (Invitrogen). The resulting fluorescent reporter plasmid was used to generate Flp-In fluorescent reporter cells and maintained according to the supplier's instructions (Invitrogen). AICAR (100~250 μM), *G. inflata* or *C. longa* extract (1.5~15 mg/mL), AMGZ (40~400 μM), or licochalcone A (0.3~3 μM) was added to the medium for 24 hr. The mCherry fluorescence was analyzed using the HCA system, with excitation/emission wavelengths at 453/486 nm.

Real-Time PCR

Total RNA from 293 ATXN3 lines was extracted using Trizol reagent (Invitrogen). The RNA was DNase (Stratagene) treated, quantified, and reverse-transcribed to cDNA as described. Real-time quantitative PCR experiments were performed in the ABI PRISM® 7000 Sequence Detection System (Applied Biosystems). Amplification was performed on 100 ng cDNA with gene-specific TaqMan fluorogenic probes Hs01016719 for PPARGC1A, Hs00232352_m1 for NFE2L2, Hs01110250_m1 for HMOX1, Hs00168547_m1 for NQO1, Hs01553554_m1 for SOD2, Hs01588973_m1 for CYCS, and 4326321E for HPRT1 (endogenous control) (Applied Biosystems). Fold change was calculated using the formula $2^{\Delta Ct}$, $\Delta C_T = C_T(\text{control}) - C_T(\text{target})$, in which $C_T$ indicates cycle threshold.

Western Blot Analysis

Total proteins were prepared using lysis buffer containing 50 mM Tris-HCl pH8.0, 150 mM NaCl, 1 mM EDTA pH8.0, 1 mM EGTA pH8.0, 0.1% SDS, 0.5% sodium deoxychalate, 1% Triton X-100 and protease inhibitor cocktail (Sigma). Proteins (25 μg) were separated on 10% SDS-polyacrylamide gel electrophoresis and transferred onto nitrocellulose membranes by reverse electrophoresis. After blocking, the membrane was probed with PPARGC1A (1:500 dilution, Abcam), NFE2L2 (1:250 dilution, Santa Cruz), NQO1 (1:1500 dilution, Sigma), GCLC (1:100 dilution, Abcam), GSTP1 (1:1000 dilution, Abcam), SOD2 (1:200 dilution, Santa Cruz), CYCS (1:400 dilution, Santa Cruz) or ACTB (actin, beta; 1:5000 dilution, Millipore) at 4° C. overnight. Then the immune complexes were detected by horseradish peroxidase-conjugated goat anti-rabbit or goat anti-mouse IgG antibody (1:5000 dilution, GeneTex) and chemiluminescent substrate (Millipore).

PPARGC1A cDNA Co-Transfection

HEK-293T cells were pretreated with *G. inflata* extract for 8 hr, and co-transfected with ATXN3/$Q_{75}$-GFP and PPARGC1A-specific or control siRNA for two days. Cells were stained with Hoechst 33342 and the percentage of aggregate formation assessed by HCA system. In addition, cell lysates were prepared and analyzed with anti-PPARGC1A or anti-NFE2L2 antibody.

Reactive Oxygen Species (ROS) Analysis

293 ATXN3/$Q_{75}$-GFP cells were plated into 6-well ($5\times10^4$/well) dishes, grown for 24 hr and treated with different concentrations of the *G. inflata* extract (50 μg/mL), *C. longa* extract (50 μg/mL), AMGZ (1 μM), or licochalcone A (10 nM) for 8 hr. Then ATXN3/$Q_{75}$-GFP expression was induced and aggregate accumulated for 6 days. Fluorogenic CellROX™ Deep Red Reagent (5 μM, Molecular Probes) designed to measure ROS in live cells was added to the cells and incubated at 37° C. for 30 min. The cells were then washed with PBS and analyzed for green (GFP) and red (ROS) fluorescence on a flow cytometry (Becton-Dickinson), with excitation/emission wavelengths at 488/507 (green) and 640/665 nm (red). Each sample contained $5\times10^4$ cells.

1,1-diphenyl-2-picryl hydrazyl (DPPH) Assay

The free radical scavenging activities of tested compounds and herbal extracts were determined using the stable 1,1-diphenyl-2-picrylhydrazyl (DPPH, Sigma) free radical assay (see Li, N.; Liu, J. H.; Zhang, J.; Yu, B. Y. Comparative evaluation of cytotoxicity and antioxidative activity of 20 flavonoids. *Journal of Agricultural and Food Chemistry* 56:3876-3883; 2008) with some modifications. Briefly, radical scavenging activity was measured in an ethanol mixture containing 100 μM DPPH radical solution and tested compounds (10~200 μM) or herbal extracts (0.2~4 mg/mL) The mixture was vortexed for 15 sec and then left to stand at room temperature for 30 min. Then, the scavenging capacity was measured by monitoring the decrease in absorbance at 517 nm by a Thermo Scientific Multiskan GO Microplate Spectrophotometer. The radical scavenging activity was calculated using the formula: 1−(absorbance of sample/absorbance of control)×100%. The antioxidative activity expressed as $EC_{50}$ was defined as the concentration of the compounds required for inhibition of the formation of DPPH radicals by 50%.

Statistical Analysis

For each set of values, data were expressed as the means±standard deviation (SD). Three independent experiments were performed and non-categorical variables were compared using the Student's t-test. All P-values were two-tailed, with values of P<0.05 considered significant.

Results

Figure 1B:
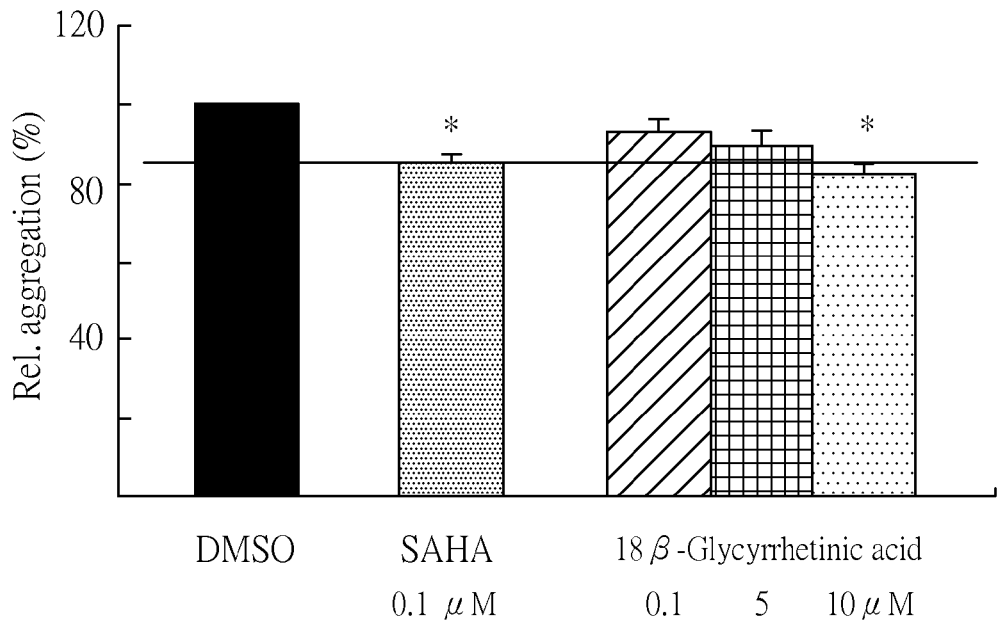
FIG. 1b shows the aggregation analysis of ATXN3/$Q_{75}$-GFP cells untreated or treated with 18β-glycyrrhetinic acid and SAHA according to a preferable example of the present invention.

Example 1 *G. inflata* Extract and its Constituents Reduce ATXN3/$Q_{75}$ Aggregation on 293 Cell Model An ATXN3/$Q_{75}$ cell model was used to test *G. inflata* extract and its constituents for their potentials to reduce the ATXN3/$Q_{75}$ aggregation. HDAC (histone deacetylase) inhibitor, SAHA, known to reduce SDS-insoluble polyQ aggregates and extract of *C. longa* were included for comparison. As a positive control, SAHA reduced the ATXN3/$Q_{75}$ aggregation to 85% (at 100 nM) as compared to untreated cells (FIG. 1a). Additional to good aggregation-inhibitory potential seen with *C. longa* extract (81~83% at 10~1500 μg/mL), *G. inflata* (80~85% at 5~500 μg/mL), AMGZ (78~83% at 0.1~100 μM) and licochalcone A (80~84% at 1~100 nM) also had greater aggregation reduction potential than SAHA. The $IC_{50}$ cytotoxicity/effective (reduced the ATXN3/$Q_{75}$ aggregation to 85% or lower) dose ratio of SAHA, extract of *C. longa*, extract of *G. inflata*, AMGZ and licochalcone A were 3800, >3000, 5300, >10000, and $3\times10^5$, respectively. Considering 5~500 μg/ml of *G. inflata* extract contained 0.13~12.5 μM AMGZ and 1~100 nM licochalcone A and tested greatest aggregation reduction potential of 0.1~100 μM for AMGZ and 1~100 nM for licochalcone A, both AMGZ and licochalcone A can be regarded as a major active component for the aggregation inhibition in *G. inflata*. Besides, treatment with 18β-glycyrrhetinic acid (81% at 10 μM) also showed better aggregation-inhibitory potential as compared with SAHA treatment (FIG. 1b).

Figure 1C:
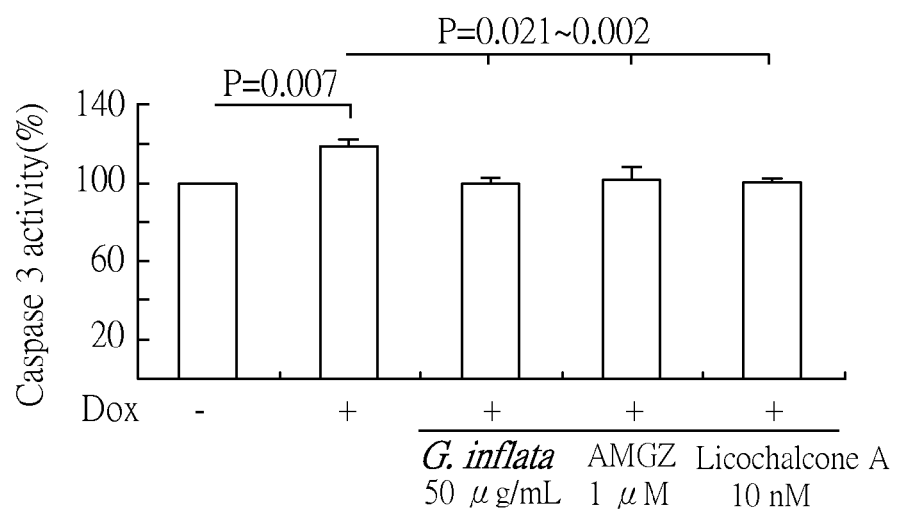
FIG. 1c shows the caspase 3 activity analysis of ATXN3/$Q_{75}$-GFP cells untreated or treated with *G. inflata*, AMGZ and licochalcone A according to a preferable example of the present invention.

The protective effect of *G. inflata* and its components against polyQ toxicity was further examined using caspase 3 activity assay after inducing ATXN3/$Q_{75}$-GFP expression for 6 days. As shown in FIG. 1c, while significantly increased caspase 3 activity was seen in cells with ATXN3/$Q_{75}$-GFP expression induced for 6 days (+Dox) as compared to non-induced cells (119% vs. 100%, P=0.007), treatment of *G. inflata* (50 μg/mL), AMGZ (1 μM), and licochalcone A (10 nM) significantly reduced caspase 3 activity (99~102% vs. 119%, P=0.021~0.002) as compared to untreated cells.

Figure 2A:
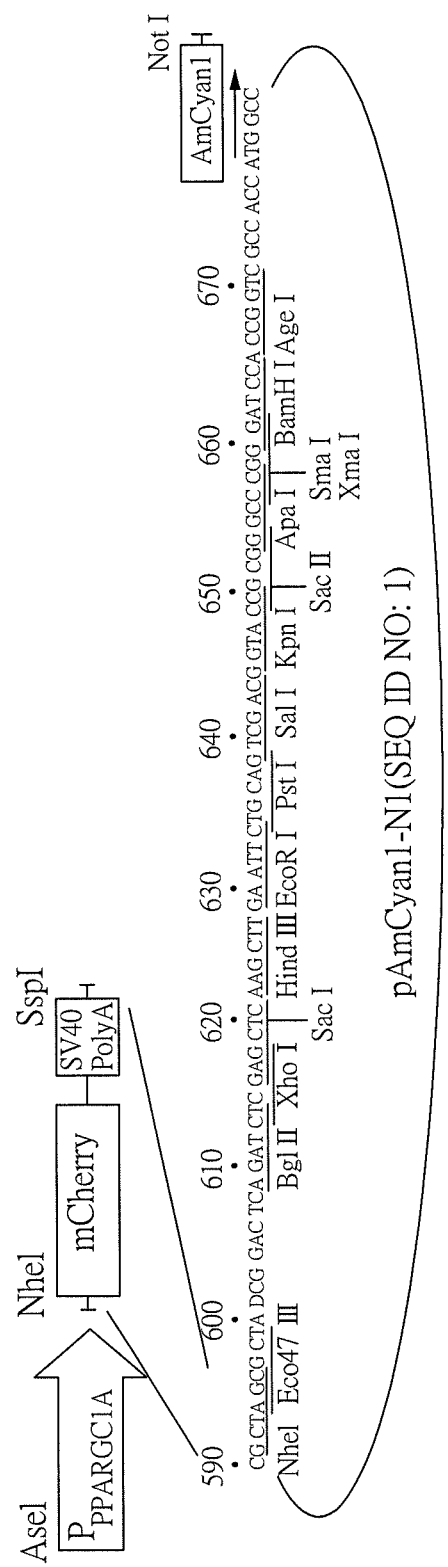
FIG. 2a demonstrates a fluorescent reporter plasmid with PPARGC1A promoter fragment upstream of mCherry reporter according to a preferable example of the present invention.
Figure 2B:
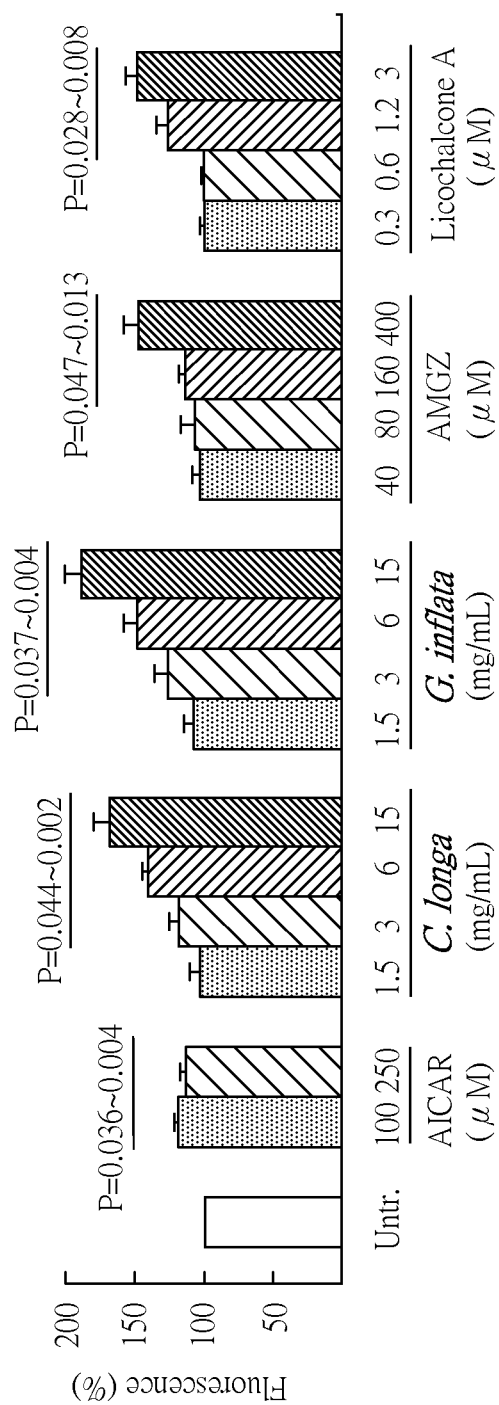
FIG. 2b shows the effect of AICAR (5-aminoimidizole-4-carboxamide-1-beta-D-riboside, Sigma), *C. longa*, *G. inflata*, AMGZ and licochalcone A on PPARGC1A reporter according to a preferable example of the present invention.

Example 2 *G. inflata* Extract and its Constituents Enhance PPARGC1A Expression on 293 Cells A fluorescent reporter 293 cell model with mCherry reporter downstream of PPARGC1A promoter (FIG. 2a) was established to examine the potential of *G. inflata* extract and its constituents to enhance PPARGC1A expression. As shown in FIG. 2b, treatment of AICAR (100~250 μM), an AMPK activator that increases PPARGC1A mRNA expression, for one day significantly increased PPARGC1A promoter activity (119~113%, P=0.004~0.036). This is also true for *C. longa* (3~15 mg/mL), *G. inflata* (3~15 mg/mL), AMGZ (160~400 μM) and licochalcone A (1.2~3 μM) treatments, with 118~169% (P=0.044~0.002), 126~190% (P=0.037~0.004), 113~147% (P=0.047~0.013) and 126~148% (P=0.028~0.008) of PPARGC1A promoter activities compared to no treatment.

Figure 3A:
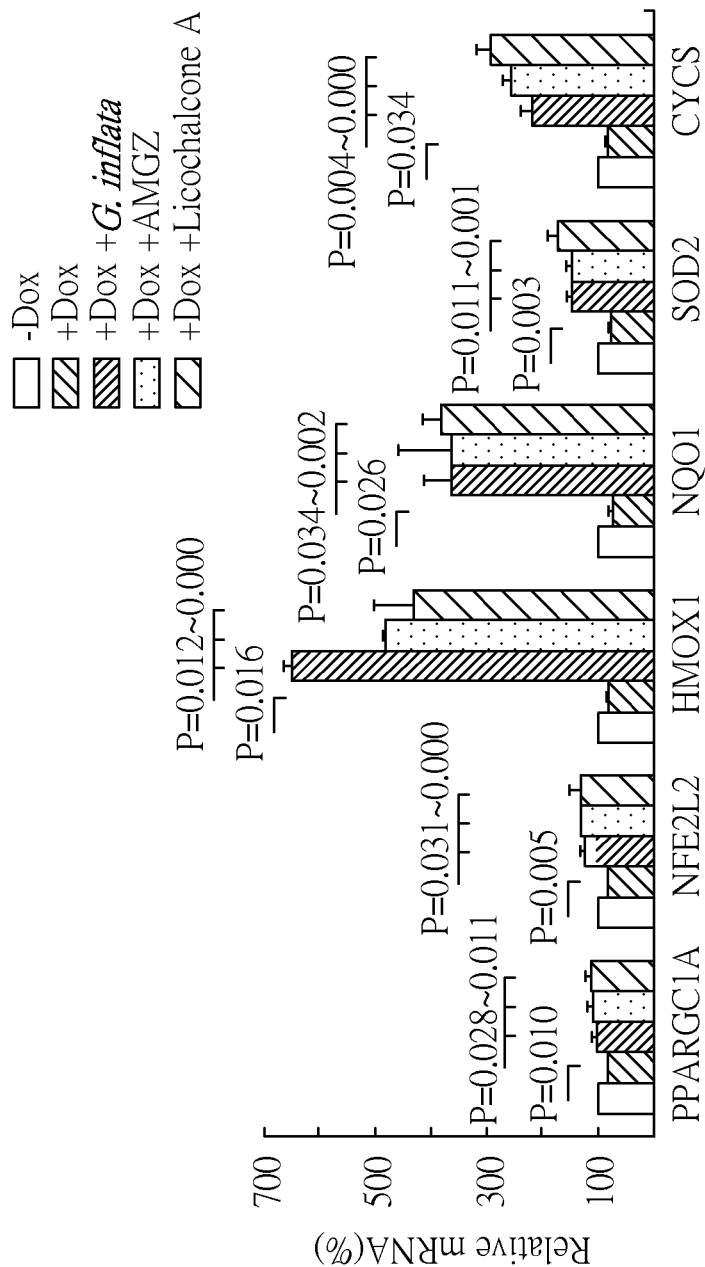
FIG. 3a shows that relative PPARGC1A, NFE2L2, HMOX1, NQO1, SOD2 and CYCS RNA levels were analyzed by real-time quantitative PCR using gene-specific fluorogenic probes according to a preferable example of the present invention.

Example 3 *G. inflata* Extract and its Constituents Enhanced PPARGC1A, NFE2L2, HMOX1, NQO1, SOD2, CYCS, GCLC and GSTP1 Expression on 293 ATXN3/$Q_{75}$ Cell Model To examine if AMGZ, licochalcone A and *G. inflata* extract up-regulated the PPARGC1A and downstream genes functioning in mitochondria biogenesis and antioxidation in ATXN3/$Q_{75}$ 293 cells, we compared the mRNA expression levels of PPARGC1A, NFE2L2, HMOX1, NQO1, SOD2 and CYCS between with and without AMGZ/licochalcone A/G. inflata and/or Dox treatment. As shown in FIG. 3a, induced expression of ATXN3/$Q_{75}$ for 6 days significantly attenuated the mRNA expression of PPARGC1A (83%, P=0.010), NFE2L2 (83%, P=0.005), HMOX1 (79%, P=0.016), NQO1 (74%, P=0.026), SOD2 (76%, P=0.003) and CYCS (85%, P=0.034). This reduction can be rescued by the addition of G. inflata (500 μg/mL), AMGZ (1 μM) or licochalcone A (10 nM), with significantly increased PPARGC1A (104~113%, P=0.028~0.011), NFE2L2 (123~133%, P=0.031~0.000), HMOX1 (432~649%, P=0.012~0.000), NQO1 (361~383%, P=0.034~0.002), SOD2 (146~173%, P=0.011~0.001) and CYCS (221~293%, P=0.044~0.000) mRNA expressions.

Figure 3B:
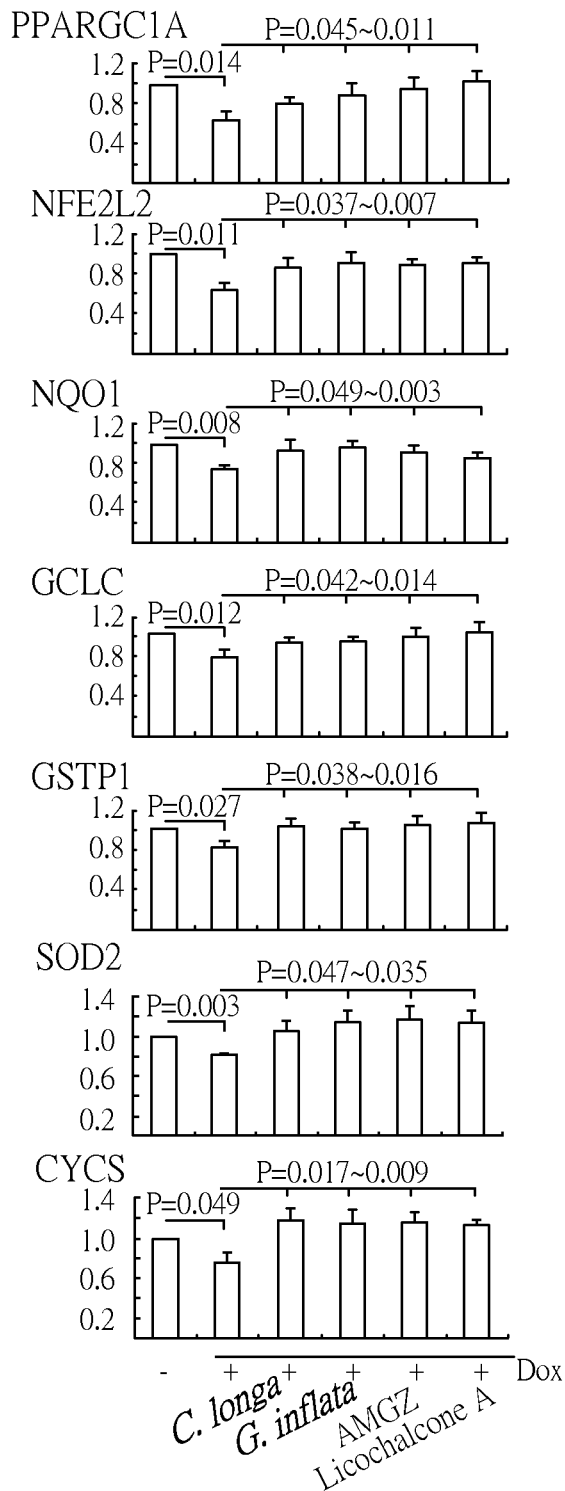
FIG. 3b shows that relative PPARGC1A, NFE2L2, NQO1, GCLC, GSTP1, SOD2 and CYCS protein levels were analyzed by immunoblot using specific antibodies according to a preferable example of the present invention.

In addition, we also examined protein expression levels of PPARGC1A, NFE2L2, NQO1, GCLC, GSTP1, SOD2, and CYCS between with and without AMGZ/licochalcone A/G. inflata/C. longa and/or Dox treatment. Similar to mRNA levels, protein expressions of PPARGC1A (63%, P=0.014), NFE2L2 (64%, P=0.011), NQO1 (75%, P=0.008), GCLC (79%, P=0.012), GSTP1 (81%, P=0.027), SOD2 (81%, P=0.003) and CYCS (76%, P=0.049) were attenuated with induced expression of ATXN3/$Q_{75}$ for 6 days and addition of C. longa, G. inflata, AMGZ or licochalcone A rescued the reduction: PPARGC1A (80~101%, P=0.045~0.001), NFE2L2 (87~92%, P=0.037~0.007), NQO1 (87~98%, P=0.049~0.003), GCLC (92~102%, P=0.042~0.014), GSTP1 (99~105%, P=0.038~0.016), SOD2 (106~117%, P=0.047~0.036) and CYCS (114~118%, P=0.017~0.009) (FIG. 3b). These findings indicated that AMGZ, licochalcone A and G. inflata up-regulated PPARGC1A and downstream NFE2L2, HMOX1, NQO1, SOD2, CYCS, GCLC and GSTP1 expressions to reduce ATXN3/$Q_{75}$ aggregation in ATXN3/$Q_{75}$ cell model.

Figure 4:
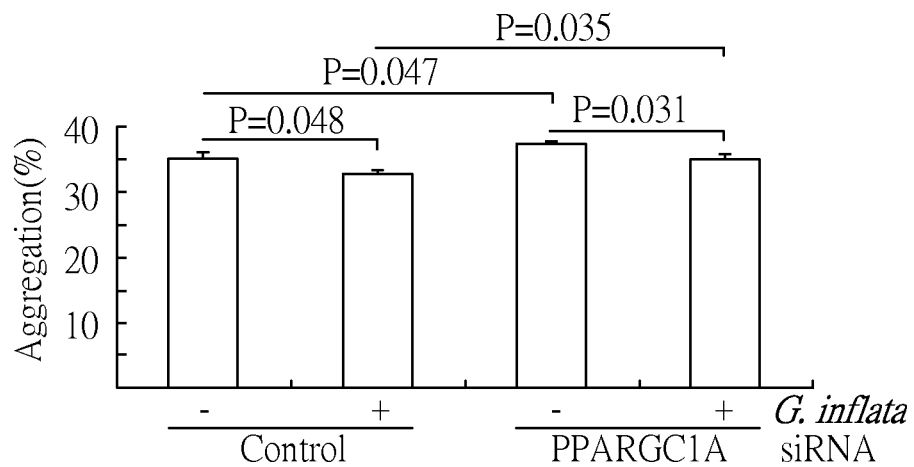
FIG. 4 shows reduced PPARGC1A expression resulted in increased ATXN3/$Q_{75}$ aggregation and *G. inflata* extract treatment decreased visible aggregates according to a preferable example of the present invention.

Example 4 Increased ATXN3/$Q_{75}$ Aggregation Upon Attenuated PPARGC1A Expression To determine whether reduced PPARGC1A expression increased aggregation of mutant ATXN3, we transiently co-expressed PPARGC1A siRNA with ATXN3/$Q_{75}$ in HEK-293T cells. As a result, co-transfection of PPARGC1A-specific siRNA attenuated PPARGC1A protein expression to 84% and NFE2L2 protein expression to 75%. Known-down of PPARGC1A significantly increased visible aggregates in ATXN3/$Q_{75}$ cells (37.2% vs. 35.0%, P=0.047) and it also attenuated the aggregate-inhibitory effect of G. inflata (34.9% vs. 32.8%, P=0.035). Treatment of G. inflata extract also significantly decreased visible aggregates in control (32.8% vs. 35.0%, P=0.048) or PPARGC1A (34.9% vs. 37.2%, P=0.031) siRNA transfected ATXN3/$Q_{75}$ cells (FIG. 4).

Figures 5A, 5B:
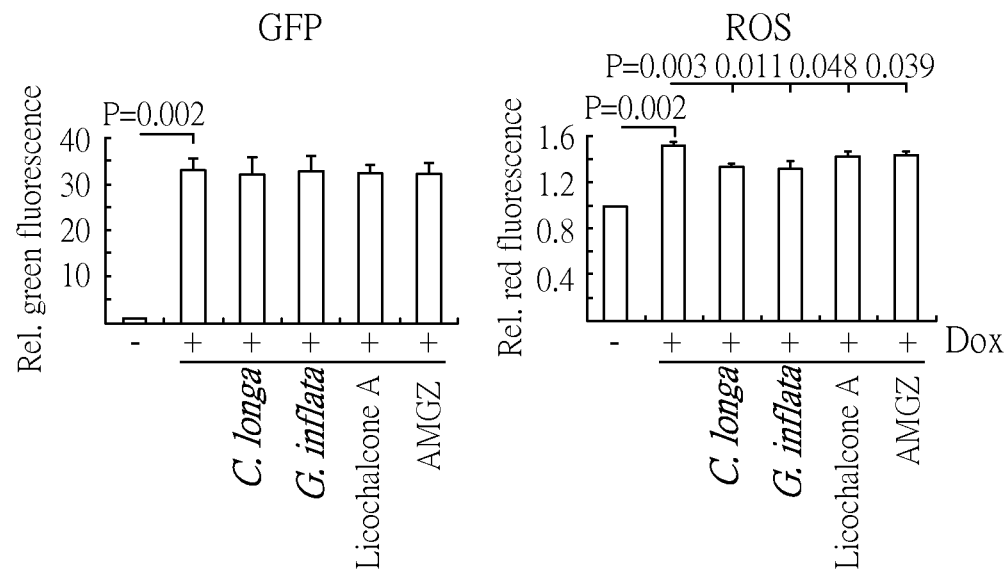
FIG. 5a shows the induced ATXN3/$Q_{75}$-GFP fluorescence expression of 293 cells treated with AMGZ, licochalcone A, and the aqueous extract of *G. inflata* or *C. longa* according to a preferable example of the present invention.
FIG. 5b shows the prevention of the induction of ROS by AMGZ, licochalcone A, and the aqueous extract of *G. inflata* or *C. longa* in ATXN3/$Q_{75}$-GFP 293 cells according to a preferable example of the present invention.

Example 5 G. inflata Extract and its Constituents Reduced ROS Production on 293 ATXN3/$Q_{75}$ Cell Model To evaluate whether AMGZ, licochalcone A and G. inflata, C. longa extracts reduced ROS formation in 293 ATXN3/$Q_{75}$ cells, the cellular production of ROS was measured by using a red fluorescent probe from Molecular Probes. As shown in FIGS. 5a-5b, induced expression of ATXN3/$Q_{75}$ (+Dox) for 6 days (32.9 folds expression) significantly increased ROS production (151%, P=0.002). With the similar induced green fluorescence (32.1~32.9 folds, P=0.738~0.918), AMGZ, licochalcone A and G. inflata, C. longa extracts significantly ameliorated oxidative stress induced by ATXN3/$Q_{75}$ (red fluorescence from 151% to 132~143%, P=0.048~0.003).

Figure 6:
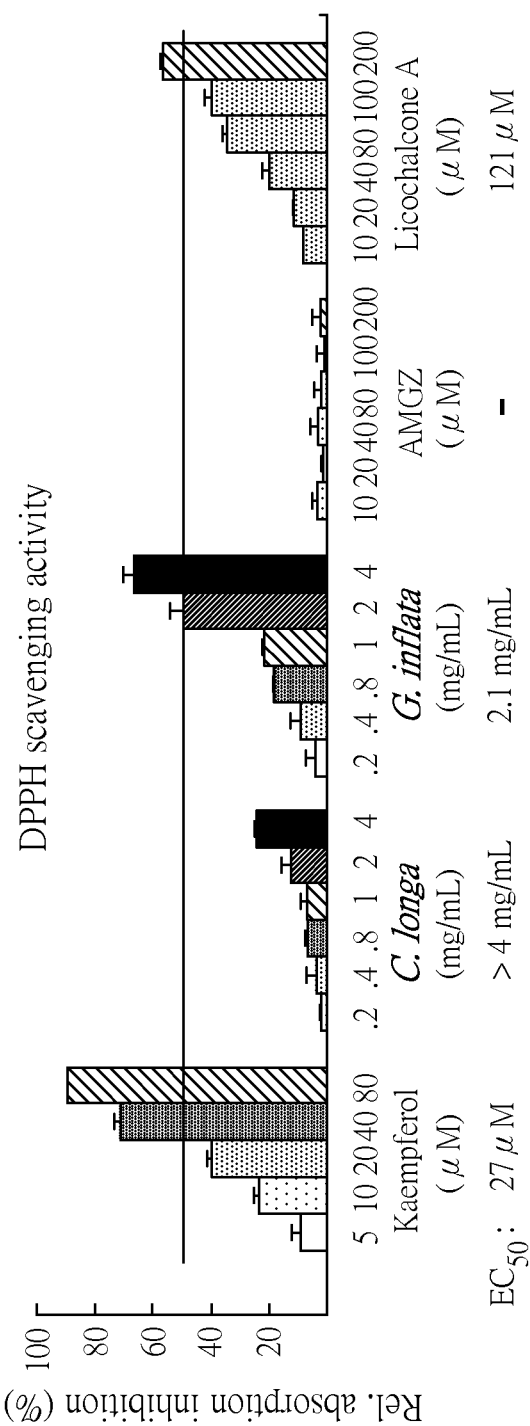
FIG. 6 shows the comparative radical scavenging activity of kaempferol, *C. longa* and *G. inflata* extracts, AMGZ and licochalcone A on DPPH according to a preferable example of the present invention.

Example 6 Radical Scavenging Activity of G. inflata Extract and its Constituents The DPPH radical is a stable organic radical with an absorption band in 517 nm. In the presence of antioxidants, the radical decolorizes from purple to yellow. We examined the scavenging activity of AMGZ, licochalcone A and G. inflata, C. longa extracts on DPPH. Kaempferol, a natural flavonol with strong antioxidant property, was chosen as the reference antioxidant for this test. The $EC_{50}$ values of the DPPH scavenging activity were calculated. As shown in FIG. 6, while no detectable DPPH scavenging activity was seen with AMGZ, C. longa, G. inflata, and licochalcone A had an $EC_{50}$ of 27 μM, >4 mg/mL, 2.1 mg/mL and 121 μM, respectively.

Figure 7A:
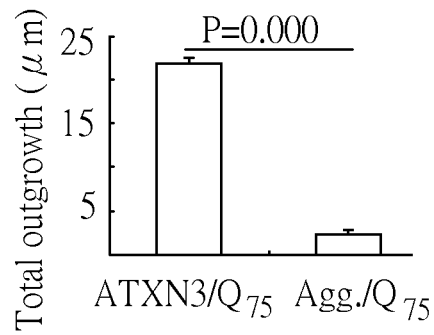
FIGS. 7a-7d shows the aggregated neuronal SH-SY5Y ATXN3/$Q_{75}$ cells with less total outgrowth, processes, and branches compared to nonaggregated cells and reduction of aggregation by the aqueous extract of *G. inflata* and its active constituents according to a preferable example of the present invention.
Figure 7B:
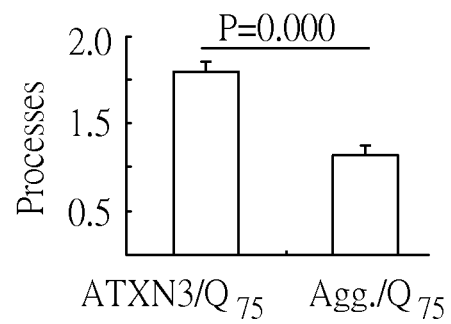
Figure 7C:
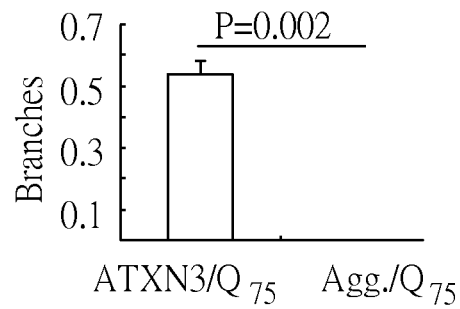
Figure 7D:
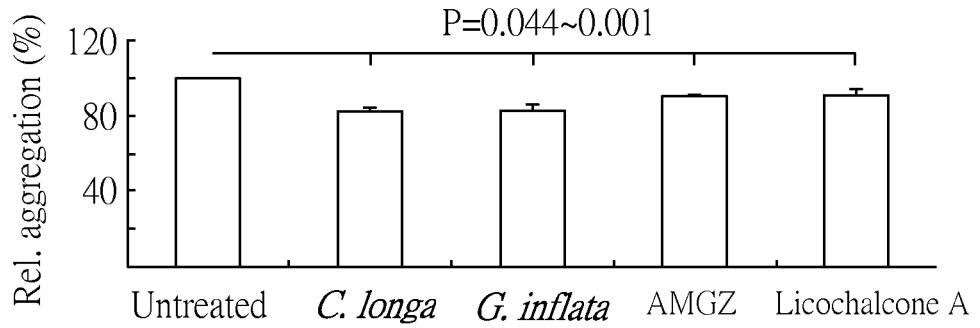

Example 7 G. inflata Extract and its Constituents Reduced ATXN3/$Q_{75}$ Aggregation on SH-SY5Y Cell Model To test the aggregation reduction potential of AMGZ, licochalcone A, G. inflata extract, and C. longa extract in neuronal cells, we constructed Flp-In SH-SY5Y cells with N-terminal truncated ATXN3/$Q_{14-75}$-GFP expression in an inducible fashion. GFP-tagged 40~57 kDa ATXN3/$Q_{14-75}$ protein in Dox-induced SH-SY5Y cells can be readily seen in Western blot. Then we differentiated ATXN3/$Q_{14-75}$-GFP SH-SY5Y cells using retinoic acid for one week. Whereas no aggregate was seen in ATXN3/$Q_{14}$-GFP cells, the induced ATXN3/$Q_{75}$-GFP formed aggregates in 1~2% differentiated neurons (data not shown). For ATXN3/$Q_{75}$-GFP expressing cells, aggregated cells showed significantly less total outgrowth (2.44 μm vs. 21.90 μm, P=0.000), processes (1.16 vs. 2.12, P=0.000), and branches (0.04 vs. 0.54, P=0.002) compared to non-aggregated cells (FIGS. 7a-7c). Treatment of G. inflata extract (10 μg/mL), C. longa extract (10 μg/mL), licochalcone A (2 nM), and AMGZ (0.2 μM) led to 18%, 17%, 10%, and 9% of aggregation reduction, respectively (P=0.044~0.001) in ATXN3/$Q_{75}$ expressed neuronal cells (FIG. 7d). These results demonstrated the aggregation-inhibitory effect of AMGZ, licochalcone A, G. inflata, and C. longa on differentiated neurons.

Although the present invention has been explained in relation to its preferred embodiment, it is to be understood that many other possible modifications and variations can be made without departing from the spirit and scope of the invention as hereinafter claimed.

What is claimed is:

1. A method for inhibiting neuronal cell aggregation in a subject in need thereof, comprising administering or contacting one or more neuronal cells within the subject with an effective amount of a *Glycyrrhiza inflata* (*G. inflata*) extract, wherein the subject is suffering from spinocerebellar ataxia (SCA) types 1, 2, 3, 6, 7, 8, 17, dentatorubropallidoluysianatrophy (DRPLA), or Huntington's disease (HD).

2. The method of claim 1, wherein the subject is a human.

3. The method of claim 1, wherein the *Glycyrrhiza inflata* (*G. inflata*) extract comprises ammonium glycyrrhizinate (AMGZ) or licochalcone A.

4. The method of claim 3, wherein the *Glycyrrhiza inflata* (*G. inflata*) extract comprises ammonium glycyrrhizinate (AMGZ).

5. The method of claim 3, wherein the *Glycyrrhiza inflata* (*G. inflata*) extract comprises licochalcone A.

6. The method of claim 1, wherein the effective amount of *Glycyrrhiza inflata* (*G. inflata*) extract is 5~500 µg.

7. The method of claim 4, wherein the effective amount of ammonium glycyrrhizinate (AMGZ) is 0.1~100 µM.

8. The method of claim 5, wherein the effective amount of licochalcone A is 0.001~0.1 µM.

9. The method of claim 1, wherein the inhibiting neuronal cell aggregation is mediated through enhanced PPARGC1A expression.

10. The method of claim 9, wherein the enhanced PPARGC1A expression up-regulates the downstream NFE2L2, HMOX1, NQO1, SOD2, CYCS, GCLC and GSTP1 expressions.

11. The method of claim 10, wherein up-regulation of NFE2L2, HMOX1, NQO1, SOD2, CYCS, GCLC and GSTP1 expressions mediates mitochondrial biogenesis.

12. The method of claim 1, wherein the inhibiting neuronal cell aggregation is mediated through reduced reactive oxygen species (ROS) production.

13. The method of claim 12, wherein the reduced ROS production is mediated through the radical scavenging activity of the *Glycyrrhiza inflata* (*G. inflata*) extract.

14. The method of claim 1, wherein the neuronal cell aggregation is poly-Q mediated.

15. The method of claim 1, wherein the subject suffers from spinocerebellar ataxia (SCA).

16. The method of claim 15, wherein the subject suffers from spinocerebellar ataxia (SCA) type 3.

* * * * *

SEQUENCE LISTING

<160> NUMBER OF SEQ ID NOS: 1

<210> SEQ ID NO 1
<211> LENGTH: 94
<212> TYPE: DNA
<213> ORGANISM: Artificial sequence
<220> FEATURE:
<223> OTHER INFORMATION: Synthesized plasmid

<400> SEQUENCE: 1

```
cgctagcgct adcggactca gatctcgagc tcaagcttga attctgcagt cgacggtacc    60
gcgggcccgg gatccaccgg tcgccaccat ggcc                                94
```